United States Patent
Sherman et al.

(10) Patent No.: US 7,785,330 B2
(45) Date of Patent: Aug. 31, 2010

(54) METHOD AND APPARATUS FOR DISTAL TARGETING OF LOCKING SCREWS IN INTRAMEDULLARY NAILS

(75) Inventors: Jason T. Sherman, Leesburg, IN (US); Mark R. DiSilvestro, Columbia City, IN (US); Radivoje S. Popovic, St-Sulpice (CH)

(73) Assignee: DePuy Products, Inc., Warsaw, IN (US)

( * ) Notice: Subject to any disclaimer, the term of this patent is extended or adjusted under 35 U.S.C. 154(b) by 414 days.

(21) Appl. No.: 11/518,775

(22) Filed: Sep. 11, 2006

(65) Prior Publication Data
US 2008/0086145 A1 Apr. 10, 2008

(51) Int. Cl.
A61B 17/58 (2006.01)
A61B 17/60 (2006.01)
A61F 2/00 (2006.01)
A61B 19/00 (2006.01)
A61B 5/05 (2006.01)

(52) U.S. Cl. .................. 606/96; 606/98; 606/104; 606/130; 600/424

(58) Field of Classification Search .................. 606/64, 606/96–98, 104, 130; 600/424
See application file for complete search history.

(56) References Cited

U.S. PATENT DOCUMENTS

| | | | | |
|---|---|---|---|---|
| 4,621,628 A | * | 11/1986 | Brudermann | 606/97 |
| 5,049,151 A | | 9/1991 | Durham et al. | |
| 5,127,913 A | * | 7/1992 | Thomas, Jr. | 606/62 |
| 5,411,503 A | * | 5/1995 | Hollstien et al. | 606/86 R |
| 5,514,145 A | | 5/1996 | Durham et al. | |
| 5,584,838 A | * | 12/1996 | Rona et al. | 606/96 |
| 5,707,375 A | | 1/1998 | Durham et al. | |
| 6,162,228 A | | 12/2000 | Durham | |
| 6,168,595 B1 | | 1/2001 | Durham et al. | |
| 6,211,666 B1 | * | 4/2001 | Acker | 324/207.17 |
| 6,503,249 B1 | * | 1/2003 | Krause | 606/62 |
| 6,754,609 B2 | * | 6/2004 | Lescourret | 702/150 |
| 2004/0034355 A1 | * | 2/2004 | Govari et al. | 606/72 |
| 2005/0075562 A1 | * | 4/2005 | Szakelyhidi et al. | 600/424 |
| 2005/0080427 A1 | * | 4/2005 | Govari et al. | 606/98 |
| 2007/0161888 A1 | | 7/2007 | Sherman et al. | |
| 2008/0086145 A1 | * | 4/2008 | Sherman et al. | 606/97 |

FOREIGN PATENT DOCUMENTS

| | | |
|---|---|---|
| EP | 1382308 | 1/2004 |
| EP | 1520535 | 4/2005 |
| WO | WO 9713467 A1 * | 4/1997 |
| WO | 0134016 | 5/2001 |

OTHER PUBLICATIONS

European search report in a corresponding European application (i.e. EP 07 25 3589), dated Dec. 19, 2008 (3 pages).

* cited by examiner

*Primary Examiner*—Thomas C Barrett
*Assistant Examiner*—Christian Sevilla
(74) *Attorney, Agent, or Firm*—Maginot, Moore & Beck

(57) ABSTRACT

A system that enables targeting of an instrument placed within a drill bushing aligns the axis of a drill bushing with the axis of a transverse hole in an intramedullary nail. The system includes a probe having an elongated member with a distal end, a magnet that is polarized along its longitudinal axis that is mounted perpendicularly to the distal end of the elongated member; and a processor executing programmed instructions to determine a position and orientation of the magnetic sensor array with respect to the targeting magnet.

11 Claims, 6 Drawing Sheets

METHOD AND APPARATUS FOR DISTAL TARGETING OF LOCKING SCREWS IN INTRAMEDULLARY NAILS

CROSS-REFERENCE TO RELATED APPLICATIONS

Reference is made to commonly-assigned co-pending U.S. patent application Ser. No. 11/323,537, filed on Dec. 30, 2005, entitled "Method For Determining A Position Of A Magnetic Source," the disclosure of which is hereby expressly incorporated in its entirety by reference.

TECHNICAL FIELD

The present invention relates generally to systems for aligning locking screws with openings in intramedullary nails, and more particularly, to such systems that use magnetic fields to align the locking screws with a transverse opening in an intramedullary nail.

BACKGROUND

Systems for aligning locking screws in intramedullary nails to secure fractured bones together are known. These systems may be broadly categorized into three classes: x-ray imaging systems, mechanical systems, and electromagnetic systems. X-ray imaging systems use x-ray imaging to provide an image of the limb being treated with the inserted intramedullary nail so the surgeon may view the transverse hole located in the nail. This image facilitates the surgeon's locating the proper position on the external surface of the bone for drilling and aligning the drill bit with the transverse hole. Once the correct drill position and alignment are determined, the x-ray imaging system is removed so the surgeon may then drill a hole through the bone that passes through the hole in the nail. These x-ray imaging systems expose the patient and the surgeon to x-rays and the accumulation of x-rays, especially for the surgeon, may have long-term detrimental consequences.

The mechanical systems require reference points so the offset distance from the reference point may be externally determined and viewed by the surgeon to correlate a path through a bone to the opening of the hole in the intramedullary nail. Studies have shown, however, that an intramedullary nail may undergo some lateral and dorsal deformation as well as some rotational movement. Mechanical systems are not able to track these movements accurately and inconsistent targeting may occur as a result.

Systems that have previously used electromagnetic or magnetic components for aligning a drill for boring a hole in a bone so the drill bit passes through the transverse hole suffer from a number of limitations. Some systems of this type require that a magnet be mechanically located within the transverse hole of the nail. A pivotally mounted magnet is placed on the bone surface and moved until the magnet aligns with the dipole within the nail. This position may then be marked for drilling, but the angular orientation of the drill must be maintained by the surgeon without further reference to the external dipole that was removed for the drilling operation.

Other electromagnetic systems, such as the one disclosed in U.S. Pat. No. 5,584,838 or U.S. Pat. No. 4,621,628, use one or more electromagnetic drive coils and a plurality of electromagnetic flux sensors to guide alignment of a drill bushing with the transverse hole in an intramedullary nail. These systems measure the current or voltage induced in magnetic pick up coils associated with a drill bushing by a drive coil that is located within a medullary canal to determine the alignment of the drill bushing axis with the axis of the transverse hole. The design, development, and manufacture of these systems, however, are difficult. Additionally, some of these systems require the drive coil to be removed from its location within the transverse hole so that the drilling operation may be performed without boring through the drive coil. When the drive coil is removed from the transverse hole the coil sensors no longer generate signals that may be used to align the drill bushing. Consequently, the surgeon must maintain the proper orientation and placement of the drill without any indicia to confirm correct placement of the drill.

A system that addresses some issues arising from the use of electro-magnetic targeting devices is disclosed in published application US 2005/0075562. The system in this published application uses a permanent, cylindrical magnet that is mounted to the end of a rod so the longitudinal axis of the magnet is aligned with the rod. The magnet is designed to have a magnetic field that is axisymmetric. Such a magnet is made by polarizing a cylindrical magnet through its diameter rather than along its longitudinal axis. The magnet is placed within an intramedullary nail at a position just short of a transverse hole in the nail. An elliptical array of magnetoresistive (MR) elements is mounted in fixed relation to one or more drilling sleeves. The MR elements are composed of material that changes its electrical resistance in response to magnetic flux passing through a sensor element. The MR elements are coupled together in a Wheatstone bridge arrangement so that the voltage output of the bridge is zero when the array is in a position where the plane of the sensor array is parallel to the plane through the longitudinal center plane of the magnet and the center of the sensor array is over the center of the magnet.

The system in the published application suffers from the use of the MR elements. While these elements are sensitive to changes in magnetic flux, they are not always consistent in their responses. Specifically, these elements have a tendency to experience hysteresis. Consequently, an MR element may produce one resistance at a given magnetic field strength and then produce a different resistance at the same magnetic field strength as the magnetic field strength is varied between measurements. Variations in magnetic field strength are common as a surgeon moves and rotates the sensor array to locate the zero point. In order to compensate for any hysteresis experienced by the magnetic sensor elements, the sensor array is frequently reset.

Frequent resetting also confirms that the reading generated by the sensor array arises from the magnetic field generated by the magnet within the intramedullary nail. Environmental magnetic fields may affect the reading generated by the sensor array because MR elements are sensitive to very small changes in magnetic field strength. Resetting the array is thought to be beneficial because as the sensor array is brought closer to the bone, the magnetic field generated by the magnet in the bone dominates. The earth's magnetic field, however, does vary as a function of time and spatial orientation in the vicinity of the patient's bone. Consequently, it may affect the reading generated by the sensor array even when the array is reset.

SUMMARY

A system is described below that addresses the need for a targeting system that is more tolerant of magnetic noise without requiring the sensor array to be reset frequently. A system that enables targeting of an instrument placed within a drill bushing aligns the axis of a drill bushing with the axis of a transverse hole in an intramedullary nail. The system includes a probe having an elongated member with a distal end, a magnet that is polarized along its longitudinal axis that is mounted perpendicularly to the distal end of the elongated member; and a processor executing programmed instructions to determine a position and orientation of the magnetic sensor array with respect to the targeting magnet.

The system includes a probe having an elongated member with a distal end and a magnet that is polarized along its longitudinal axis and having a circular cross-section that is mounted perpendicularly to the distal end of the elongated member, and a targeting array of magnetic sensors located outside a patient's body and each magnetic sensor generating a signal that is approximately equal to a signal generated by the magnetic sensor located at a symmetric position in the targeting array in response to the targeting array being centered on the longitudinal axis of the magnet and the plane of the targeting array being parallel to the cross-section of the magnet.

The above described features and advantages, as well as others, will become more readily apparent to those of ordinary skill in the art by reference to the following detailed description and accompanying drawings.

DETAILED DESCRIPTION

Figure 1:
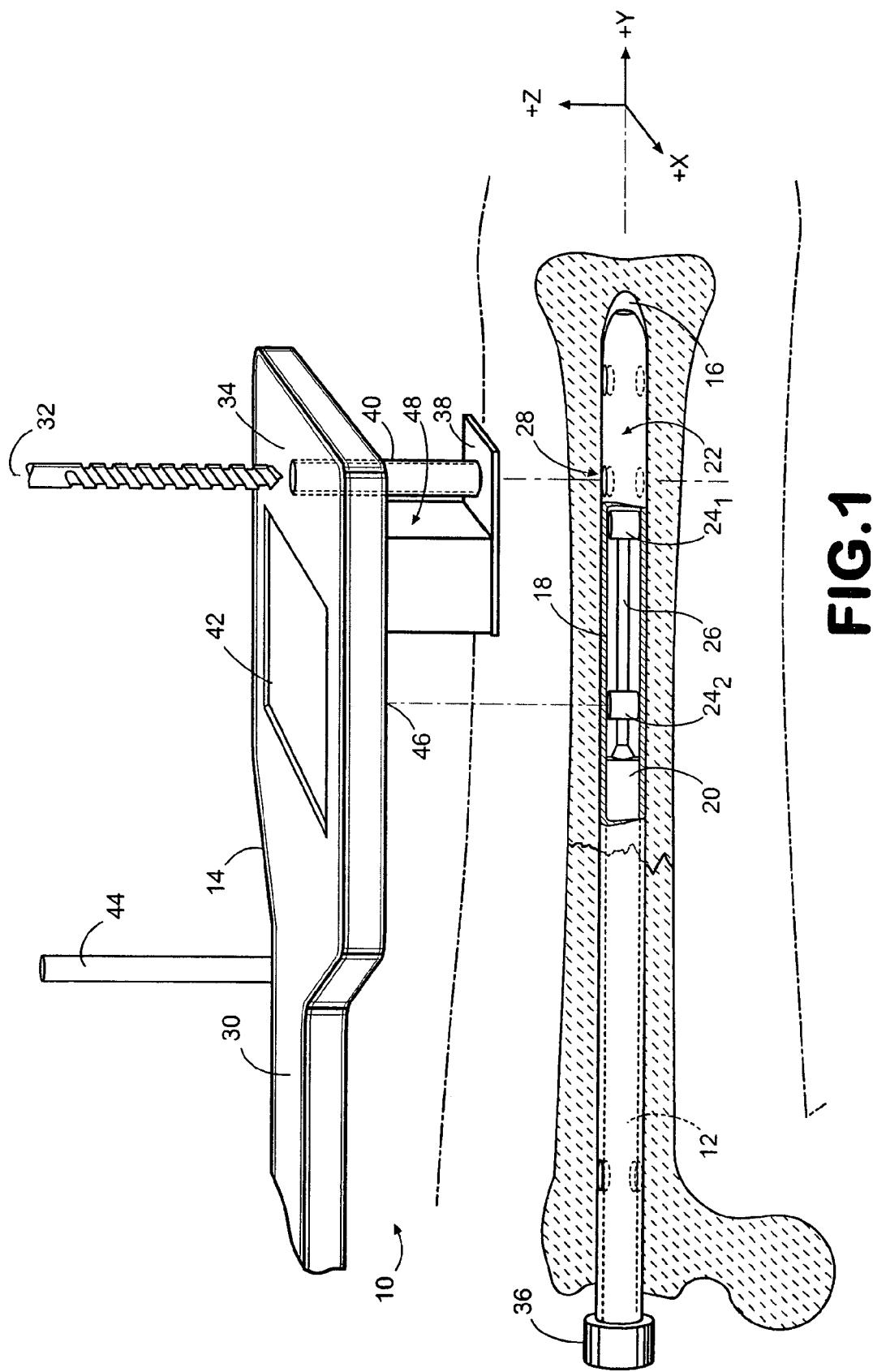
FIG. 1 is a perspective view of a system made in accordance with the principles of the present invention to perform intramedullary nail hole targeting.

An embodiment of a system 10 for determining the target point of a drill within a drill bushing is shown in FIG. 1. System 10 is comprised of a probe 12 and a handheld guide 14. Probe 12 is comprised of an elongated member 20 to which a pair of magnets $24_1$, $24_2$ is mounted. The elongated member 20 may be comprised of a rod 26 and a sheath 18 of plastic material so that the probe 12 may be inserted in interior passageway 16 of an intramedullary nail 22. Alternatively, the magnets $24_1$, $24_2$ may be mounted to the end of the rod 26 without a covering sheath. Intramedullary nails are well-known in the orthopaedic field for securing broken bone fragments to one another. FIG. 1 is not drawn to scale as the handheld unit is not longer than a femur. The dimensions of the various system components and bone shown in FIG. 1 have been altered to depict all of the system components and their environment.

The handheld guide 14 includes a display 42, a drill bushing 40, and a support 48. Handheld guide 14 also includes a hand grip 30 that may be formed as an extension of or mounted to an upper platform and circuit housing 34. Alternatively, hand grip 30 may be integrally formed with or mounted to lower platform 38. Other configurations for providing a hand grip may be used as well. A drill bushing 40 having an axis 32 extends from upper platform 34 to lower platform 38 to guide the path of scalpels, drill bits, or screwdrivers. A printed circuit board is contained within the circuit housing 34 of the handheld guide 14. The electronics for generating the target display and the battery for powering the electronics are mounted on the printed circuit board. Bottom support 38 holds the bottom of the drill bushing 40 so the axis 32 through the bushing 40 remains perpendicular to the bottom support 38.

A vertical extension 44 is also provided with the housing 34. The extension 44 may be integrally formed or mounted to the handheld unit 14. The extension includes a magnetic sensor, such as the ones discussed in more detail below. The extension 44 holds the magnetic sensor out of the magnetic field emanating from the targeting magnets so the sensor measures background magnetic fields in the vicinity of the handheld unit 14. These measurements are used to remove the effects of these background magnetic fields discussed in more detail below.

An adjustable positioning jig 36 is provided to establish a reference position for locating the probe 12 within the nail 22 so the most distal magnet 24 is in the proper position for targeting the transverse hole 28. In one embodiment, jig 36 is a sliding collar through which the probe 12 extends. The probe is inserted into the intramedullary nail while the nail is outside the patient. The probe is extended through the collar to a position where the magnet 24 is aligned with the transverse hole 28 or is parallel to the hole at a position offset in the Y direction from the hole. The spatial relationship between the sliding collar and the probe 12 is then marked to establish the length to which the probe is to be inserted once the nail is placed within the medullary canal of a patient's bone. The sliding collar may be selectively fixed at a location on the probe in a known manner.

The magnets 24 may be an off-shelf permanent magnet made of Neodymium Iron Boron (NdFeB), for example. The magnet must have a length that fits within the space between the entrance and exit of transverse hole 28. In order to track six degrees of freedom with the seventeen magnetic sensor array described below, two magnets $24_1$, $24_2$ may be mounted to the rod 26 so each magnet forms a T with rod 26. That is, the longitudinal axis of each magnet $24_1$, $24_2$ may be perpendicular to the longitudinal axis of the rod 26. Other arrangements of the magnets may be used as long as the magnetization axis of the magnet is perpendicular to the rod 26. Because magnets may be magnetized independently of the magnet's geometric shape, the magnets $24_1$, $24_2$ the magnets may be mounted to the rod 26 differently than shown in FIG. 1. As depicted in the figure, one of the magnets $24_1$ is mounted to the end of the rod 26 while the rod 26 passes through the other magnet $24_2$. The magnets are oriented so their magnetization axes are parallel to one another and spaced from one another by a distance that is at least three times the longest physical dimension of the magnets. The magnets $24_1$, $24_2$ may be polarized so the north and south poles of the magnets are located along the longitudinal axis of the magnets. As a consequence, the Z axis is aligned with the longitudinal axis of the magnet, the Y axis is aligned with the longitudinal axis of the rod 26, and the X axis is aligned with the diameter of the circular cross-section of the magnets $24_1$, $24_2$ orthogonal to both the Y and the Z-axes. Although the magnets $24_1$, $24_2$ on the rod 26 are shown in FIG. 1 as being cylindrical, other shapes may be used in the various embodiments of the probe 12, such as spherical, rectangular, or variations of these shapes.

The double magnet probe enables the surgeon to properly orient the handheld unit 14 so the drill bushing is aligned with the transverse hole in the nail. If only a single magnet mounted to the distal end of the probe 12 was used, the seventeen sensor array described more fully below could sense five of the possible six degrees of freedom for the magnet. The rotation angle about the Z axis, however, could not be sensed. As a consequence, the handheld unit 14 may be rotated so that the drill bushing is not aligned with the bone at all. To prevent this type of error, the second magnet $24_2$ is provided at a distance so the field emitted by the second magnet sensed by the sensor array is much smaller than that of the first magnet. To detect the second magnet, a separate alignment sensor 46 for determining unit alignment with the probe is provided in the lower surface of the upper platform 34, although positions may be used as long as the sensor is sufficiently distant from the sensor array that its measurements are not affected by the magnet mounted at the distal end of the probe 12. When the measurement at the alignment sensor 46 is approximately zero in the X-axis and Y-axis, the handheld unit is properly oriented over the nail 22 because the center sensor of the sensor array and the alignment sensor 46 form a line that is approximately parallel to the line through the center of the two targeting magnets. Therefore, the alignment sensor enables the sixth degree of freedom to be identified for proper orientation of the handheld unit. The alignment sensor may be implemented with a single 2-axis sensor or two single axis sensors arranged orthogonal to one another.

The positioning jig 36 is used to fix the position of the magnet mounted to the rod end to be offset in the Y-axis of the transverse hole 28 at a distance that corresponds to the distance between the center sensor in the magnetic sensor array and the longitudinal axis 32 through the bushing 40. Once the center sensor of the magnetic sensor array is aligned with the magnet mounted at the end of the probe 12 and the alignment sensor is positioned over the second magnet mounted on the rod 26, then the drill bushing 40 is aligned over the transverse hole 28. Because the magnets mounted on the probe 12 are offset from the transverse hole, the drill bit does not encounter either magnet as it passes through the transverse hole.

In another embodiment, a single magnet 24 that is polarized along its longitudinal axis may be mounted to the end of the rod 26. Again, the magnet 24 is mounted to the end of the rod 26 so that its longitudinal axis is perpendicular to the longitudinal axis of the rod 26. This type of probe may be used with a magnetic sensor array comprised of sixteen magnetic sensors that does not have the central sensor of the sensor array comprised of seventeen magnetic sensors described below. With the single magnet probe, the positioning jig 36 is used to place the magnet within the transverse hole 28 and align the longitudinal axis of the magnet with the longitudinal axis of the transverse hole 28. The drill bushing 40 in this embodiment passes through the center of the magnetic sensor array. Thus, when the balance conditions are achieved for the sixteen sensors arranged about the drill bushing, the bushing is aligned with the transverse hole. The probe in this situation, however, must be withdrawn from the passageway 16 of the nail 22 or the drill bit 32 will encounter the magnet as it enters the transverse hole 28. Consequently, this embodiment may be used to orient the handheld unit and then begin the drilling until the bit alignment is established in the patient's bone. Then the probe is withdrawn so drilling may continue without risk of drilling into the magnet.

The processing of the signals generated by the sensor array described below may be performed by an application specific integrated circuit (ASIC) or general microprocessor that is coupled to appropriate support circuits. Programmed instructions for the operation of the handheld unit 14 may be stored in a non-volatile memory such as a PROM or ROM mounted on the printed circuit card. Alternatively, the programmed instructions may be stored in a portable memory unit that may be selectively coupled to the handheld guide.

The magnetic flux density at a point in space may be defined by the equation:

$$B = \begin{bmatrix} B_x \\ B_y \\ B_z \end{bmatrix}$$

$$= \frac{\mu_0 m}{4\pi r^3} \left( 3 \begin{bmatrix} x \\ y \\ z \end{bmatrix} \frac{x\sin\theta\cos\varphi + y\sin\theta\sin\varphi + z\cos\theta}{r^2} - \begin{bmatrix} \sin\theta\cos\varphi \\ \sin\theta\sin\varphi \\ \cos\theta \end{bmatrix} \right)$$

where B is the magnetic flux density, $\mu_0$ is the magnetic permeability of free space, m is the magnitude of the magnetic moment for a probe magnet, r is the radial distance from the dipole to the point (x, y, z) at which the measurement is being taken, and θ is the rotation angle from the +Z-axis towards the +X-axis, and ψ is the rotation angle in the XY plane. This equation accurately describes the magnetic flux density at a point provided that the radial distance r is substantially larger than the radius of the magnet.

Figure 2:
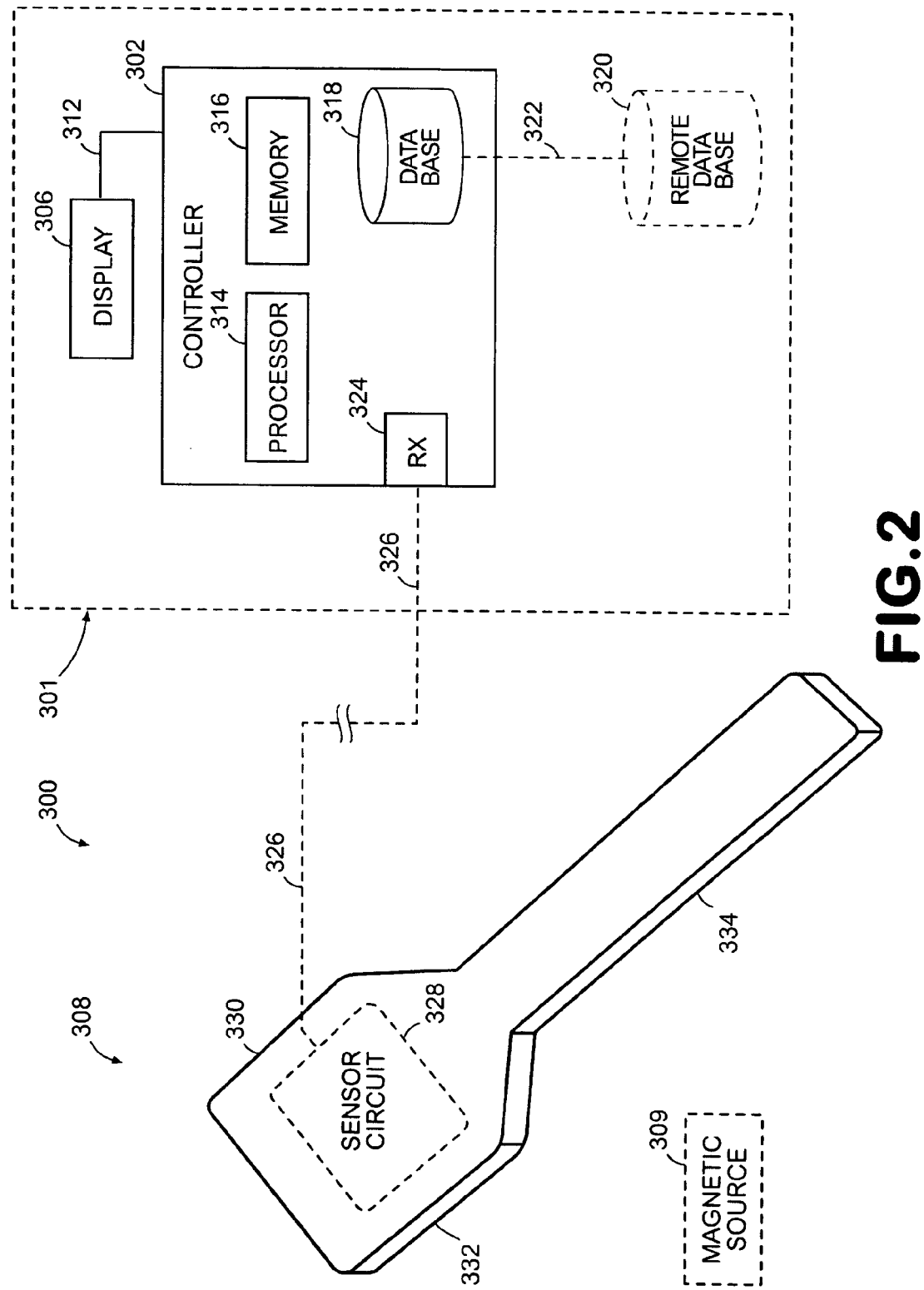
FIG. 2 depicts a block diagram of the guidance unit shown in the system of FIG. 1.

One embodiment of a targeting system is shown in FIG. 2. The targeting system 300 includes a magnetic sensing unit 308 and a guidance unit 301. Within the magnetic sensing unit 308 is a magnetic sensing array 328 that includes magnetic sensing elements arranged and operated in a manner described in more detail below. Each of these magnetic sensing elements generates an electrical signal in response to magnetic flux density passing through the element. These signals may be quantized as data and transmitted to the guidance unit 301 for processing with an identifier of the element that generated the signal. The guidance unit 301 processes these data representing flux density to determine the angular orientation and spatial position of the magnetic source 309 that produced the flux lines with respect to the sensor array elements.

While the guidance unit 301 is depicted in FIG. 2 as being external to the magnetic sensing unit 308, it may be incorporated within the unit 308. In this embodiment, a display is visible on the upper surface of the unit 308. Also in this embodiment, the signal from a diametrically opposed element is compared with a signal generated by an element to determine angular orientation and spatial position of the elements. These signal comparisons may be used to generate directions to the surgeon, either textually or graphically, as to how the sensing head 332 should be moved to align the sensor array in the head 332 with the magnetic source 309.

In more detail, the guidance unit 301 includes a controller 302 and a display 306. The controller 302 is communicatively coupled with the display device 306 via a communication link 312. Although illustrated in FIG. 2 as separate from the controller 302, the display device 306 may form a portion of the controller 302 in some embodiments. Additionally, in some embodiments, the display device 306 may be positioned away from the controller 302. For example, the display device 306 may be coupled with a ceiling or wall of the operating room in which the orthopaedic surgical procedure is being performed. Additionally or alternatively, the display device 306 may be embodied as a virtual display such as holographic display, a body mounted display such as a heads-up display, or the like. The controller 302 may also be coupled with a number of input devices such as a keyboard and/or a mouse. However, in the illustrative embodiment, the display device 306 is a touch-screen display device capable of receiving inputs from a surgeon using the guidance unit 301. That is, the surgeon can provide input data to the display device 306 and controller 302, such as making a selection from a number of on-screen choices, by simply touching the screen of the display device 306.

The controller 302 may be embodied as any type of controller including, but not limited to, a computer such as a personal computer, a specialized microcontroller device, a collection of processing circuits, or the like. The controller 302 includes a processor 314 and a memory device 316. The processor 314 may be embodied as any type of processor including, but not limited to, discrete processing circuitry and/or integrated circuitry such as a microprocessor, a microcontroller, and/or an application specific integrated circuit (ASIC). The memory device 316 may include any number of memory devices and any type of memory such as random access memory (RAM) and/or read-only memory (ROM). Although not shown in FIG. 2, the controller 302 may also include other circuitry commonly found in a computer system.

The controller 302 may also include a database 318. The database 318 may be embodied as any type of database, electronic library, and/or file storage location. For example, the database 318 may be embodied as a structured database or as an electronic file folder or directory containing a number of separate files and an associated "look-up" table. Further, the database 318 may be stored on any suitable device. For example, the database 318 may be stored in a set of memory locations of the memory device 316 and/or stored on a separate storage device such as a hard drive or the like.

Additionally or alternatively, the controller 302 may be coupled to a remote database 320 via a communication link 322. The remote database 320 may be similar to the database 318 and may be embodied as any type of database, electronic library, and/or a file storage location. The remote database 320 may be located apart from the controller 302. For example, the controller 302 may be located in an orthopaedic surgery room while the remote database 318 may form part of a hospital network and be located in a separate room or building apart from the orthopaedic surgery room. As such, the communication link 322 may be embodied as any type of communication link capable of facilitating data transfer between the controller 302 and the remote database 320. For example, in some embodiments, the communication link 322 may form a portion of a network such as a Local Area Network (LAN), a Wide Area Network (WAN), and/or a global, publicly-accessible network such as the Internet.

The controller 302 also includes a receiver or transceiver 324. The receiver 324 is used by the processor 314 to communicate with the magnetic sensor array 308 via a communication link 326. The communication link 326 may be embodied as any type of communication link capable of transmitting data from the magnetic sensor array 308 to the controller 302. For example, the communication link 326 may be a wired or wireless communication link and use any suitable communication technology and/or protocol to transmit data. As such, the receiver 324 may be embodied as any type of receiver capable of facilitating communication between the controller 302 and the magnetic sensor array 308 including, for example, a wired or wireless receiver.

The illustrative magnetic sensing unit 308 of the embodiment shown in FIG. 2 includes a housing 330 having a sensing head portion 332 and a handle 334 coupled to the head portion 332. The handle 334 may be used by a user of the system 300, such as an orthopaedic surgeon, to move and position the magnetic sensor array 308. The magnetic sensor array 308 also includes a sensor circuit 328 located in the head portion 332. As discussed in more detail below, the sensor circuit 328 is configured to sense a magnetic field generated by the magnetic source 309 and determine data indicative of a position of the magnetic source 309 relative to the magnetic sensor array 308. Such data may be transmitted via the communication link 326 and receiver 324 to the controller 302 for processing or used to generate directions to a surgeon that are displayed at the unit 308. As used herein, the term "position" is intended to refer to any one or more of the six degrees of freedom which define the location and orientation of a body (e.g., the magnetic source 309) in space or relative to a predetermined point or other body.

Figure 3:
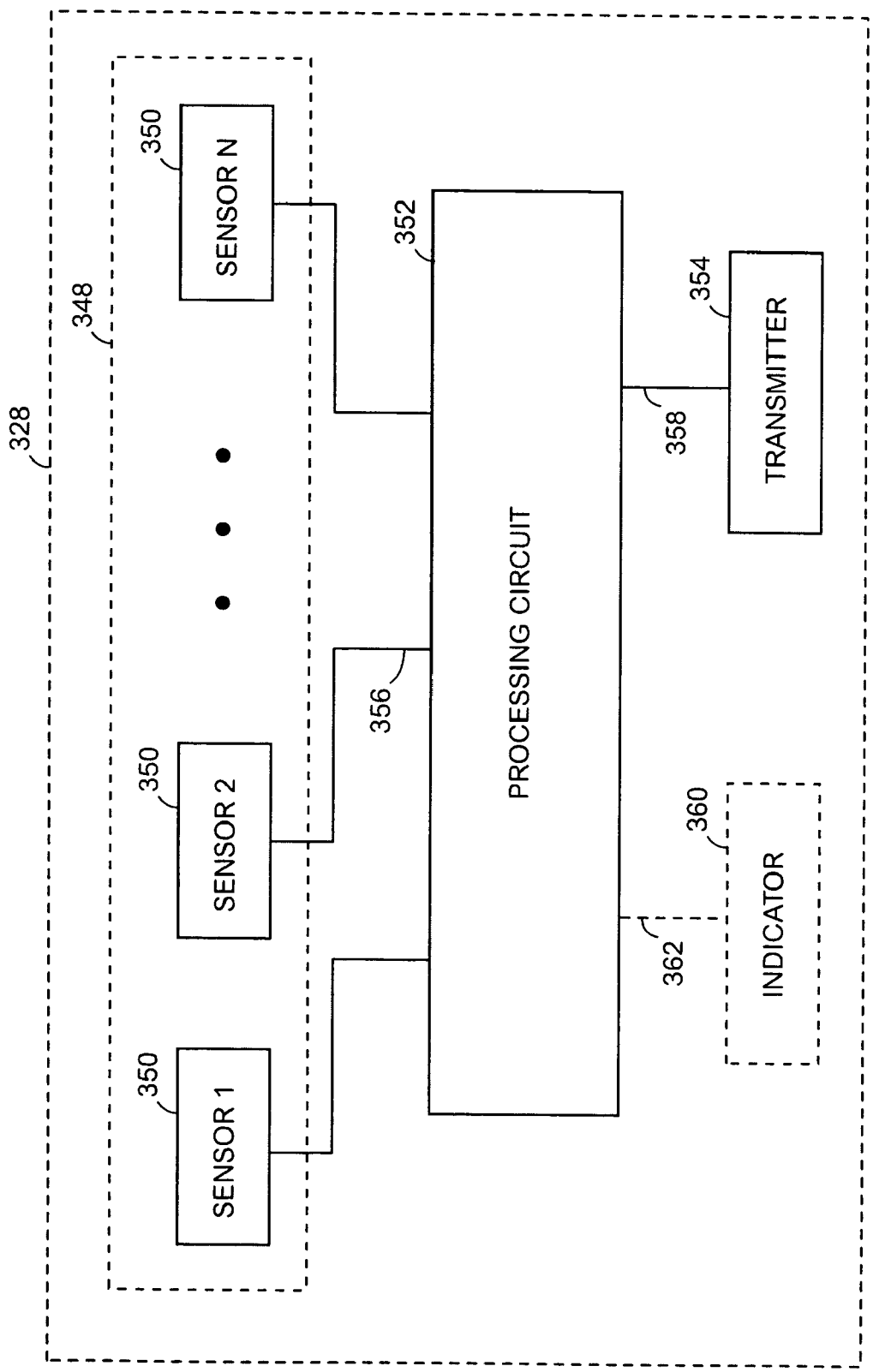
FIG. 3 is a block diagram of the magnetic sensor array depicted in FIG. 2.

To sense the magnetic field(s) of the magnetic source 309, the sensor circuit 328 includes a magnetic sensor arrangement 348 that may be arranged as illustrated in FIG. 3. The magnetic sensor arrangement 348 includes one or more magnetic sensors 350. The sensor circuit 328 also includes a processing circuit 352 and a transmitter 354. The magnetic sensors 350 are electrically coupled to the processing circuit 352 via a number of interconnects 356. The processing circuit 352 is also electrically coupled to the transmitter 354 via an interconnect 358. The processing circuit 352 is also electrically coupled to an indicator 360 via an interconnect 362. The interconnects 356, 358, and 362 may be embodied as any type of interconnects capable of providing electrical connection between the processing circuit 352, the sensors 350, the indicator 360, and the transmitter 354, such as, for example, wires, cables, PCB traces, or the like.

The number of magnetic sensors 350 that form the magnetic sensor arrangement 348 may depend on such criteria as the type of magnetic sensors used, the material, size, and strength of the magnet used, the specific application, and/or the configuration of the magnetic sensor array 308. For example, the magnetic sensors 350 are configured to measure a three-dimensional magnetic field of the magnetic source 309. As such, the sensor circuit 328 may include any number and configuration of one-dimensional, two-dimensional, and/or three-dimensional magnetic sensors such that the sensor circuit 328 is capable of sensing or measuring the magnetic field or the magnetic source 309 in three dimensions. Additionally, the magnetic sensor(s) 350 may be embodied as any type of magnetic sensor capable of sensing or measuring the magnetic field generated by the magnetic source 309. For example, the magnetic sensors 350 may be embodied as superconducting quantum interference (SQUID) magnetic sensors, anisotropic magnetoresistive (AMR) magnetic sensors, giant magnetoresistive (GMR) magnetic sensors, Hall-effect magnetic sensors, or any other type of magnetic sensors capable of sensing or measuring the three-dimensional magnetic field of the magnetic source. In one particular embodiment, the magnetic sensor(s) are Hall effect sensors designated as X-H3X-xx_E3C-25HX-2.5-0.2T or X-H3X-xx_E3C-25HX-2.5-20 mT Three Axis Magnetic Field Transducers, which are commercially available from SENIS GmbH, of Zurich, Switzerland. Regardless, the magnetic sensors 350 are configured to produce a number of data values (e.g., voltage levels) which define one or more of the components (e.g., X—, Y—, and Z-components) of the three-dimensional magnetic flux density of the magnetic field of the magnetic source 309 at the point in space where each sensor is located and in the orientation of each sensor's active sensing element. These data values are transmitted to the processing circuit 352 via the interconnects 356.

Figure 4:
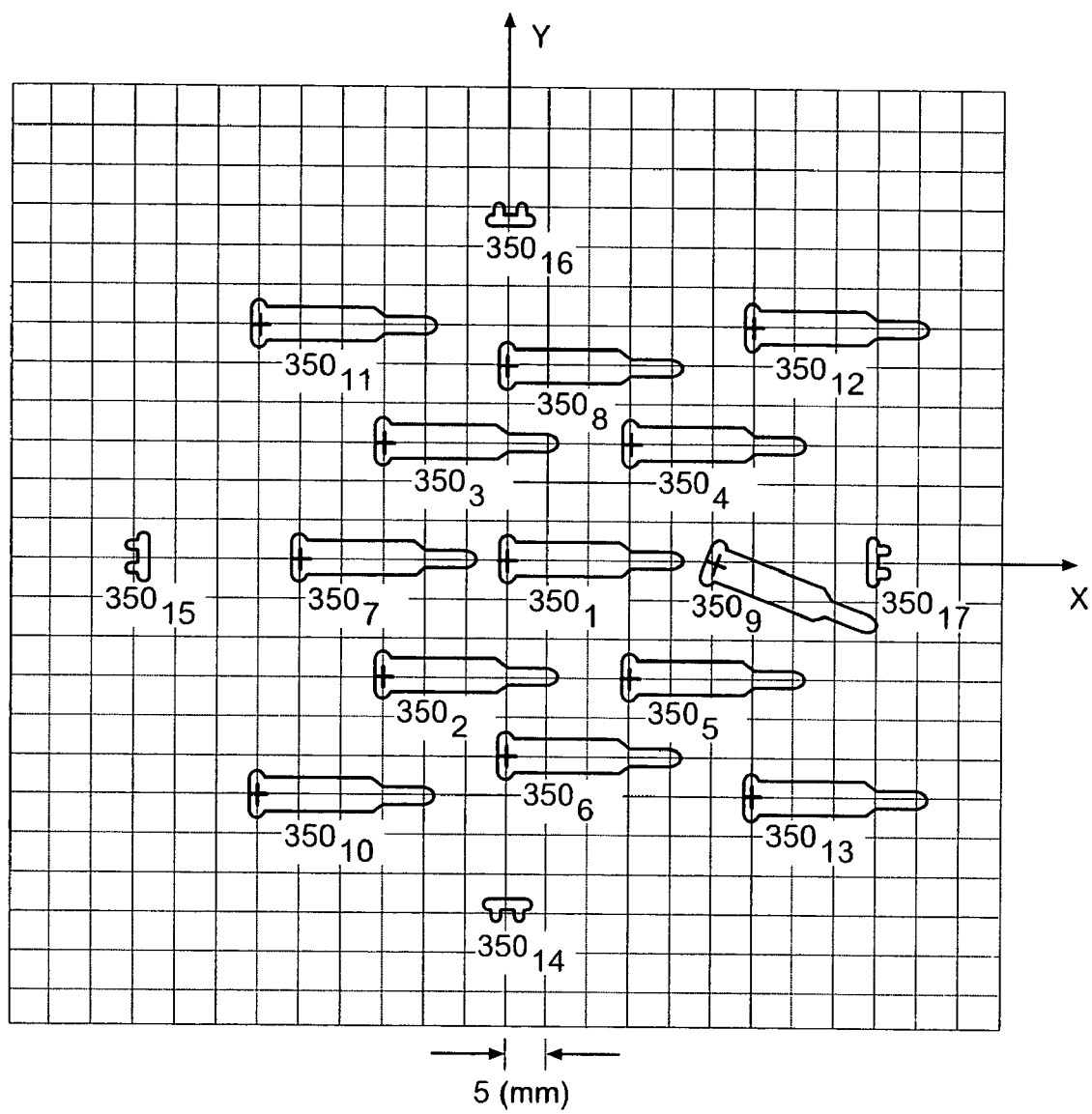
FIG. 4 is top plane view of a sensor board populated with magnetic sensing elements to implement an exemplary magnetic sensor array.

To provide a targeting system that is not subject to the hysteresis experienced by anisotropic magnetoresistive (AMR) magnetic sensors, the magnetic sensor arrangement 348 uses Hall effect magnetic sensors that are arranged in a pattern, such as the one shown in FIG. 4. Although the sensors are depicted as being arranged in a plane, other configurations are possible including volumetric arrangements in which one or more of the sensors may overlap other sensors in the Z direction. In the exemplary embodiment shown in FIG. 4, the sensor arrangement 348 includes seventeen magnetic sensors $350_1$-$350_{17}$. The magnetic sensors $350_1$-$350_{17}$ are secured to a sensor board 370 that may be formed from any non-magnetic material capable of supporting the magnetic sensors $350_1$-$350_{17}$ in the desired configuration. For example, in the illustrative embodiment, the sensor board 370 is formed from FR4. The magnetic sensors $350_1$-$350_{17}$ may be mounted on or in the sensor board 370. As such, the sensor board 370 forms the sensing face of the sensor circuit 328 and may be located inside the head portion 332 of the magnetic sensor array 308 (i.e., located behind the housing material) or mounted to the head portion 332 such that the sensor board 370 is exposed.

In one embodiment, the sensor board has a width of about 12 centimeters, a length of about 12 centimeters, and a thickness of about 2.5 centimeters. Sensor boards having other dimensions that allow the mounting of the desired number of magnetic sensors 350, however, may be used. The magnetic sensors 350 are mounted to or in the sensor board 370 according to a predetermined configuration. Each of the magnetic sensors $350_1$-$350_{17}$ may be a one dimensional, two dimensional, or three dimensional sensor. As such, each of the magnetic sensors $350_1$-$350_{17}$ may include one, two, or three active sensing elements, respectively. Each sensing element of the magnetic sensors $350_1$-$350_{17}$ is capable of measuring at least one component of the magnetic flux density of a magnetic source at the position (i.e., location and orientation) of the particular magnetic sensor. To do so, each magnetic sensor 350 includes a field sensitive point at which the magnetic flux density is measured. The configuration of the magnetic sensors $350_1$-$350_{17}$ is described below in reference to the field sensitive point of each magnetic sensor with the understanding that the body of the sensor may be positioned in numerous orientations wherein each orientation facilitates the same location of the field sensitive point.

The array comprised of seventeen magnetic sensors shown in FIG. 4 is arranged so that sixteen of the magnetic sensors are positioned about a centrally located seventeenth magnetic sensor. Five of the magnetic sensors are three channel magnetic sensors used for measuring magnetic flux density in three orthogonal axes and twelve of the magnetic sensors are one channel only magnetic sensors for measuring magnetic flux density individually in only one axis of a three orthogonal axis system. One of the five magnetic sensors that are three channel sensors is centrally positioned within and equidistant from the other four of the five magnetic sensors.

In more detail and as illustrated in FIG. 4, four of the magnetic sensors $350_{14}$-$350_{17}$ are located at positions that may be referred to as compass points because they lie at the 0, 90, 180, and 270 degree positions with respect to the central point $350_1$ of the array 348. Moreover, the magnetic sensors $350_{14}$ and $350_{16}$ are diametrically opposed to one another with respect to the center sensor $350_1$ as are the magnetic sensors $350_{15}$ and $350_{17}$ with respect to one another about the center sensor $350_1$. These four sensors are single channel sensors. Sensors $350_{14}$ and $350_{16}$ measure flux density in the Y direction at the field sensitive point for these sensors and the sensors $350_{15}$ and $350_{17}$ measure flux density in the X direction at the field sensitive points for these sensors. As noted above, the probe embodiment of FIG. 1 orients the magnets so that the Y-axis direction is aligned with the longitudinal axis of the rod 26 and the X-axis direction is aligned with the diameter of the circular cross-section of the magnets 24 that is perpendicular to the longitudinal axis of the rod 26.

In a similar manner, the magnetic sensor arrangement 348 also includes symmetric pairs of magnetic sensors. That is, sensors $350_6$ and $350_8$ are a pair of single channel sensors symmetrically located about the center sensor $350_1$ that measure flux density in the Z direction. Likewise, sensors $350_7$ and $350_9$ are a pair of single channel sensors symmetrically located about the center sensor $350_1$ that measure flux density in the Z direction. Sensors $350_{10}$-$350_{13}$ are equidistant from the center sensor $350_1$. Each of these sensors is a single channel sensor that measures flux density in the Z direction. The magnetic sensors $350_1$-$350_5$ are three channel sensors that measure magnetic flux in the X, Y, and Z directions. Sensors $350_2$-$350_5$ are equidistant from the center sensor $350_1$. The direction in which a sensor measures flux density depends upon the orientation of the sensor with respect to the board to which the sensors are mounted. For example, some of the magnetic sensors are positioned orthogonally to the measurement surface of the sensor board 370 while other sensors are positioned on the sensor board 370 coplanar with the measurement surface of the sensor board 370 or otherwise substantially parallel therewith.

The magnetic sensors $350_2$-$350_{17}$ are positioned on the sensor board 370 so the center sensor $350_1$ of the array 348 is aligned with the longitudinal axis of the magnetic source 309 and the plane of the array is perpendicular to the longitudinal axis of the magnet or magnets when the measurements of the sensors in the array are balanced. The measurements are balanced when the following conditions occur:

$B_{x1} \approx B_{y1} \approx 0$ $B_{x3} \approx -B_{x5}$ $B_{y2} \approx -B_{y4}$ $B_{y3} \approx 0$ $B_{y5} \approx 0$ $B_{x2} \approx 0$ $B_{x4} \approx 0$ $B_{z2} \approx B_{z3} \approx B_{z4} \approx B_{z5}$ $B_{z6} \approx B_{z7} = B_{z8} \approx B_{z9}$ $B_{z10} \approx B_{z11} \approx B_{z12} \approx B_{z13}$ $B_{y14} \approx -B_{y16}$ $B_{x15} \approx -B_{x17}$ where $B_{ij}$ represents the magnetic flux density measurement B in the i sensing direction by the jth sensor in the array depicted in FIG. 4. Although the sensors may be symmetrically arranged so the balance conditions noted above may be used. Other non-symmetrical arrangements may be used as long as the processing circuit is programmed to compensate for the non-symmetrical readings to determine position and orientation of the sensing array.

As noted above, the sensing array 348 is sensitive to five of the six degrees of freedom for the position of the magnet 24 mounted to the end of the probe 12 with respect to the array.

In order to determine the sixth degree of freedom, which in this case is the rotational angle about the Z axis, a magnetic sensor is provided in the handheld unit at a distance from the center sensor $350_1$ that corresponds to the distance between the center of the two magnets mounted to the rod 26. Identifying this alignment sensor as sensor $350_{18}$, the balance condition for this sensor that establishes proper alignment of the handheld unit 14 in the X axis is $B_{x18} \approx 0$, and in the Y axis is $B_{y18} \approx 0$. This alignment sensor may be mounted in the lower surface of the housing 34, on an extension of the printed circuit card described above, or on its own printed circuit card. The alignment sensor also needs to be oriented so its coordinate system corresponds to the coordinate system for the sensors in the array 348.

In some embodiments, the magnetic sensors 350 may have differing magnetic field sensitivities (i.e., the smallest detectable change in measured magnetic flux density) and sensing ranges. For example, in some embodiments, the magnetic sensors 350 not located at the compass points may have a lower magnetic field sensitivity but a greater sensing range than the magnetic sensors 350 located at the compass points. In one particular embodiment, the three-dimensional magnetic sensors $350_1$-$350_5$ have a magnetic sensitivity of about 50 µT (micro-Tesla) and a sensing range of about 20 mT (milli-Tesla) while the one-dimensional magnetic sensors $350_6$-$350_{17}$ have a magnetic sensitivity of about 5 µT and a sensing range of about 2 mT. In other embodiments, however, additional levels or differences of magnetic sensitivity and/or sensing range may be based on the particular distance of each magnetic sensor 350 from a predetermined location on the sensor board 370.

Because of such differences in magnetic field sensitivity and sensing range of the magnetic sensors 350, the magnetic sensor arrangement 348 may be less susceptible to positioning variances of the magnetic sensor array 348 and/or the accuracy of the magnetic flux density measurements may be improved by having magnetic sensors 350 capable of measuring the magnetic flux density of the magnetic source 309 while the magnetic sensor array is positioned close to the magnetic source 309 without going into saturation. Additionally, the magnetic sensor arrangement 348 may be less susceptible to positioning variances of the magnetic sensor array 308 and/or the accuracy of the magnetic flux density measurements may be improved by having magnetic sensors 350 capable of measuring the magnetic field of the magnetic source 309 while the magnetic sensor array 308 is positioned far from the magnetic source 309 in spite of the increase in magnetic "noise" (i.e., undesirable magnetic field effects from sources other than the magnetic source 309).

One way to improve accuracy is to measure the background magnetic fields in the vicinity of the handheld unit 14 and subtract this magnetic field "noise" from the measurements of the array sensors and the alignment sensor, in the two magnet system. To provide this capability, a magnetic sensor may be incorporated in the vertical extension 44 shown in FIG. 1. The sensor for measuring background magnetic "noise," such as the earth's magnetic field or other environmental magnetic fields, needs to be located at a distance from the magnets of the probe so that the background measuring sensor does not sense the magnetic fields emitted by the targeting magnets. Thus, the extension shown in FIG. 1, extends upwardly from the housing, which is the direction away from the targeting magnets when they are in the nail 22. Other arrangements are possible. For example, the sensor for measuring background magnetic fields may be remote from the handheld unit 14 and the measurements made by the sensor transmitted to the processing circuit in the handheld unit.

In the embodiment shown in FIG. 1, the extension may be hollow with a screw cap at its distal end. The cap may be removed so a magnetic sensor may be placed within the extension and the cap replaced. Conductors extending from the sensor traverse the length of the extension and enter the housing 34 where they are coupled through appropriate interconnects to the processing circuit. To simplify the incorporation of the background density measurements in the balance conditions, the magnetic sensor needs to be oriented so Its coordinate system is the same as the coordinate system for the array sensors. Conversion from one coordinate system to another one is possible, provided the relationship between the coordinate systems is known.

The magnetic sensor arrangement 348, discussed above, is only one illustrative embodiment and, in other embodiments, the sensor arrangement 348 of the sensor circuit 328 may include any number of magnetic sensors 350 positioned in any configuration that allows the magnetic sensors 350 to measure the three-dimensional X—, Y—, and Z-components of the measured magnetic flux density. For example, in some embodiments, the magnetic sensor arrangement 348 may include a single three-dimensional magnetic sensor. Alternatively, in other embodiments, the magnetic sensor arrangement 348 may include additional magnetic sensors 350 arranged in various configurations. By increasing the number of magnetic sensors, redundancy is developed for the sensor array. That is, magnitudes of the individual components of the measured magnetic flux densities are determined using measurements from a number of magnetic sensors 350 positioned in different locations. Thus, the accuracy of the characterization of the three-dimensional magnetic field generated by the magnetic source 309 may be increased by including additional magnetic sensors in the magnetic sensor arrangement 348.

Further, although the magnetic sensors 350 are embodied as separate magnetic sensors apart from the processing circuit 352 in the illustrative embodiment of FIGS. 2-4, in some embodiments, the magnetic sensors 350 and the processing circuit 352, or portions thereof, may be embodied as a single electronic device. For example, the magnetic sensors 350 and portions of the processing circuit 352 may be embodied as one or more complimentary metal oxide semiconductor (CMOS) device(s). By embedding the magnetic sensors 350 and processing circuit 352 in a semiconductor device, the required space of the sensor circuit 328 is reduced. Additionally, such a semiconductor device may be less susceptible to outside influences such as temperature variation of the individual magnetic sensors 350.

Figure 5:
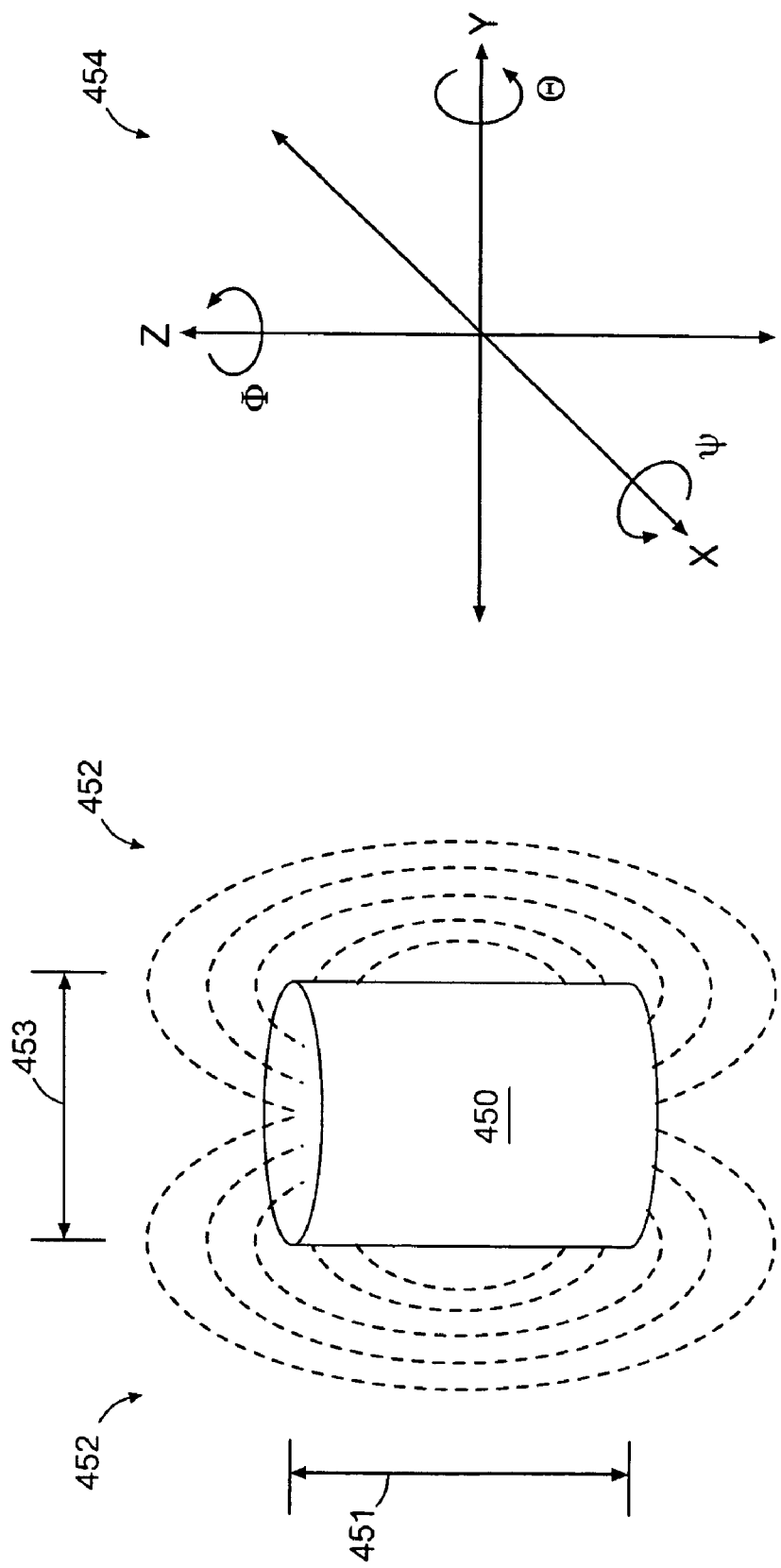
FIG. 5 is a depiction of a magnet mounted to the probe shown in FIG. 1 and a portion of the magnetic field lines representing the magnetic field emitted by the magnet.

Referring now to FIG. 5, the magnetic source 309 may be embodied as one or more magnets. In the illustrative embodiment, the magnetic source 309 is a single cylindrical, dipole magnet 450. The magnet 450 generates a magnetic field having a number of magnetic flux lines 452. Only a subset of a cross-section of generated flux lines 452 is illustrated in FIG. 5 and the flux lines (and magnetic field) circumferentially surround the magnet 450. When positioned so the axis of the magnet 450 is aligned with the longitudinal axis of a transverse hole or positioned so its longitudinal axis is parallel to the transverse hole at a known distance from the longitudinal axis of the transverse hole, the position (i.e., location and orientation) of the magnet 450 is defined by six degrees of freedom. That is, the position of the magnet 450 can be defined by three Cartesian coordinate values and three rotational values (i.e., one about each Cartesian axis). For example, as illustrated in FIG. 5 by coordinate axes 454, the position of the magnet 450 can be defined in three-dimensional space by an X-coordinate value, a Y-coordinate value, a Z-coordinate value, a (theta) θ-rotational value about the X axis, a (psi) ψ-rotational value about the Y axis, and a (phi) φ-rotational value about the Z axis.

As noted above, the probe 12 may also be configured with two magnets 24 mounted to rod 26 as shown in FIG. 1. This embodiment enables the distal magnet to be placed away from the transverse hole 28 so that the probe 12 may remain within the passageway 16 of the nail 22 during the securing of the nail within the bone. Other number of magnets and magnet configurations may be used provided the sensing array and the balance conditions are properly selected for identifying either the center of the transverse hole or a position offset from the hole by a known distance.

The magnet 450 may be formed from any magnetic material capable of generating a magnetic field of sufficient magnetic flux density or strength to be sensed or measured by the sensor circuit 328 through the relevant tissue of a patient while not exposing the patient to magnetic field strengths that do not exceed given health and safety limitations. For example, the magnet 450 may be formed from ferromagnetic, ferrimagnetic, antiferromagnetic, antiferrimagnetic, paramagnetic, or superparamagnetic material. In one particular embodiment, the magnet 450 is formed form neodymium ferrite boron (NdFeB) grade 50 alloy material. The illustrative magnet 450 is a cylindrical magnet having a length 451 of about five millimeters and a diameter 453 of about two millimeters. However, in other embodiments, magnets 450 having other configurations, such as rectangular and spherical magnets, and sizes may be used.

To improve the accuracy of the measurements of the magnetic sensors 350, the magnetic moment of a magnet 450 may be controlled during manufacture or calibrated prior to use. Only those magnets with magnetic moments on-axis or near on-axis with the magnet's longitudinal axis are transversely mounted to the end of an elongated member 20 to form a probe for the targeting system. That is, if the magnetic moment of the magnet 450 is determined to extend from the magnet 450 from a location substantially off the longitudinal axis of the magnet 450, the magnet 450 is discarded. In this way, the magnetic field generated by a magnet 450 may be sensed and measured so that the measurements of the magnetic fields and calculated values based thereon have increased accuracy.

Figure 6:
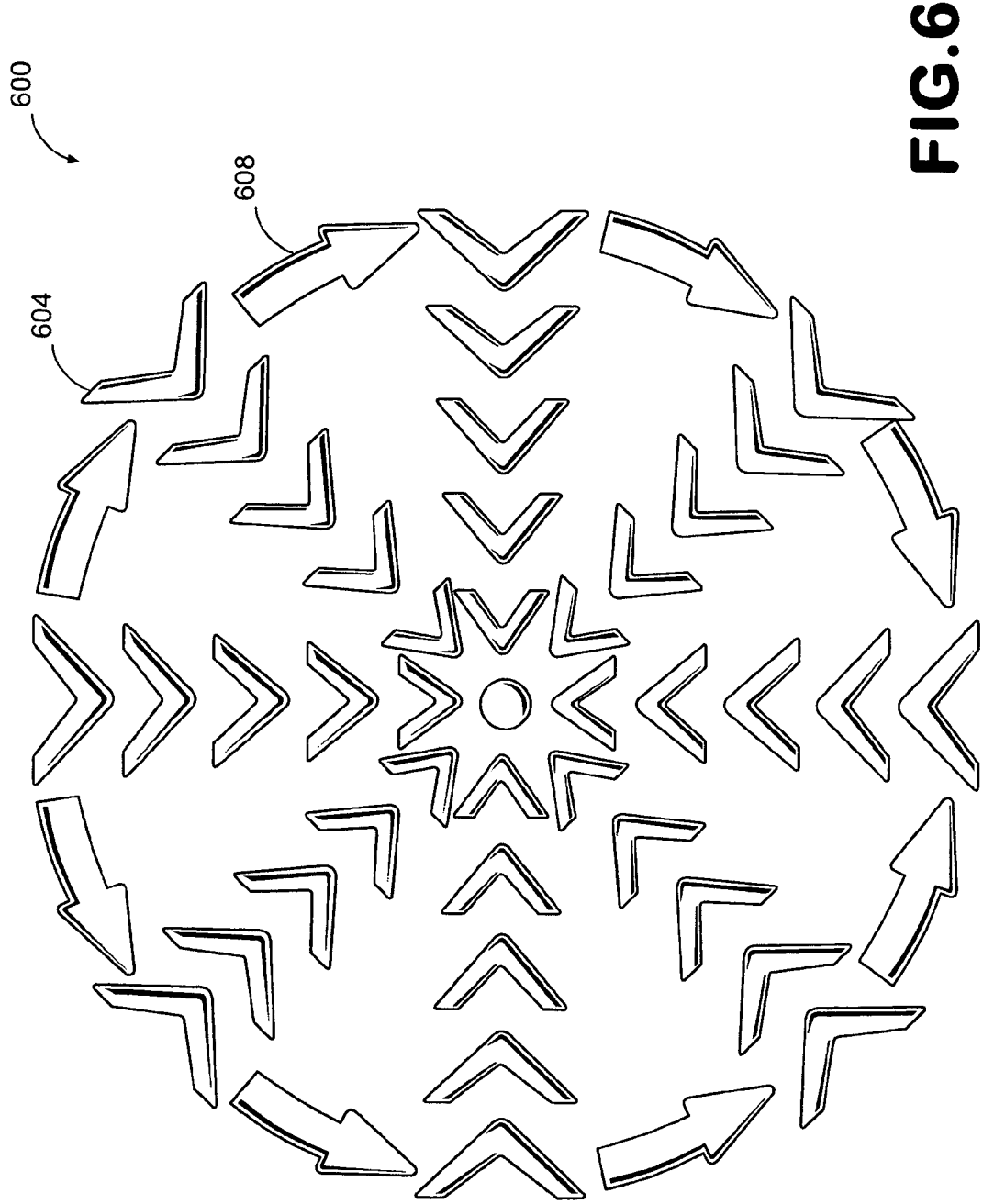
FIG. 6 is a depiction of a display for indicating the position and orientation of a magnetic sensor array with respect to a magnetic source.

A user interface, such as the display 600 shown in FIG. 6, may be used to graphically direct the surgeon to target the transverse hole in the nail. The display 600 includes chevrons 604 and arrows 608. As depicted in FIG. 6, the chevrons 604 located on the 0, 90, 180, and 270 degree positions are used to indicate translations of the handheld unit in the XY plane. The chevrons located on the 45, 135, 225, and 315 degree positions indicate roll (YZ rotation) and pitch (XZ rotation). The arrowheads 608 are used to indicate yaw (XY rotation). The display 600 may be implemented in the display 42 located on the upper surface of the handheld unit 14 in one embodiment, while it may be implemented in the display 306 in the embodiment shown in FIG. 2.

In one embodiment in which a sixteen sensor array is used, the drill bushing is located where the center sensor is located in the seventeen sensor array. The surgeon may begin the drilling in the bone for the insertion of the securing pin in the nail. Once the placement and the orientation of the hole has been established, the probe having a single magnet located within the hole is withdrawn so the drilling may proceed without risk that the drill encounters the magnet in the hole. In the embodiment in which the seventeen sensor array is used, the surgeon may continue to drill through the transverse hole without removing the probe or the handheld unit. This enables the surgeon to make continual reference to the display and verify the correct placement of the magnetic sensing array during the procedure.

To develop the empirical data set, a magnet conforming to the standards for a targeting magnet is selected and rigidly mounted to a position that simulates placement within an intramedullary nail. The sensor array is then placed in a test fixture that moves the array so the center sensor of the array is located at predetermined positions in a plane that is parallel to the plane cutting the diametrical cross-section of the magnet. This plane is located at position that approximates the distance that the sensor array is separated from the magnet during a surgical procedure. At each position, the measurements from the sensors are stored. The sensor array is also rotated by the test fixture to predetermined angular orientations of φ and ⊖ for additional measurements that are also stored. The positions selected for sensor measurements are preferably closer together and more numerous for positions near the position aligned with the center line of the magnetic field generated by the magnet. These positions are selected to correspond to changes in measurements resulting from movement of half a millimeter, if accuracy of a single millimeter is desired, for example.

Alternatively, the empirical data set may be developed by rigidly fixing the magnetic sensor array in a particular orientation and position in space. A magnet conforming to the properties for a targeting magnet is moved to predetermined positions in a plane parallel to the magnetic sensor array and tilted in various orientations to simulate positioning attitudes of the magnetic sensor array during surgical procedure use. Again, more positions are used and measured near the center of the array than at the outlying positions as accuracy at the point of true alignment is most important.

The developed empirical data set may be used to train a neural network to determine the position and orientation of the sensor array with respect to the magnet in an intramedullary nail. The neural network may be modeled using a programming language, such as MatLab, and the resulting model used develop a program in C or C++, for example. The program may then be compiled and used to control the operation of a microprocessor that operates on the measurements generated by the magnetic sensor array. Once the program is developed and stored in memory for controlling the processor, sensor measurements are input to the neural network to evaluate the "fit" of the measured data to the empirical data set to determine a position and orientation of the magnetic sensor array with respect to the targeting magnet. This determination may be used to generate the differential signals for indicating to a user the movement required to aligned the sensor array with the targeting magnet.

The empirical data set may be stored in memory for a microprocessor that determines the position of the sensor array with respect to the targeting magnet. The processor in this embodiment compares a set of sensor measurements obtained during a surgical procedure with the empirical data sets for a number of positions used in the empirical data set development. These comparisons are used to select the two positions that are closest on either side of the current data set. The actual data set is then used to interpolate a position between the two closest sets. This targeting method continues until the actual data set obtained in the surgical procedure corresponds to the aligned data set.

The use of the empirical data sets is thought to provide a number of advantages. For one, the empirical data sets act as a set of calibration values that compensate for variations in the sensitivities of the sensors and any variations in their placements within the array. Another advantage of using data sets developed from actual measurements taken during the test setup is that the actual measurements do not rely on the theoretical assumptions of the dipole assumption. Alternatively, a theoretical data set may be used instead of an empirically developed data set.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those skilled in the art. Therefore, the invention in its broadest aspects is not limited to the specific details, implementations, or illustrative examples shown and described. Accordingly, departures may be made from such details without departing from the spirit or scope of applicant's general inventive concept.

What is claimed is:

1. A system for aligning a drill bushing with a transverse hole in an intramedullary nail, the system comprising:
   a probe having an elongated member with a distal end,
   a first permanent magnet that is polarized along its longitudinal axis that is mounted perpendicularly to the distal end of the elongated member;
   a second permanent magnet polarized along its longitudinal axis and mounted about the elongated member a predetermined distance away from the first permanent magnet, the second permanent magnet being oriented about the elongated member so that its longitudinal axis is parallel to the longitudinal axis of the first magnet;
   a targeting array of magnetic sensors, each magnetic sensor in the targeting array being arranged in a single plane, each magnetic sensor in the targeting array being configured to generate magnetic flux density measurements of a magnetic field of the first permanent magnet, each magnetic sensor in the targeting array has at least one corresponding sensor in the array that indicates a balance condition when the magnetic sensor and its corresponding magnetic sensor generate magnetic flux density measurements that are approximately equal; and
   an alignment sensor spaced apart from the targeting array by approximately the predetermined distance, the alignment sensor being configured to generate magnetic flux density measurements of a magnetic field of the second permanent magnet, the predetermined distance enabling the alignment sensor to measure the magnetic flux density of the magnetic field of the second permanent magnet without the magnetic flux density measurements being affected by the magnetic field of the first permanent magnet.

2. The system of claim 1, wherein the magnetic sensors are Hall effect sensors.

3. The system of claim 1 further comprising:
   a positioning jig for fixing a position of the elongated member within an intramedullary nail so the first permanent magnet is proximate a transverse hole of the intramedullary nail.

4. The system of claim 1, the targeting array further comprising:
   sixteen magnetic sensors arranged about a drill bushing centrally located within the sixteen magnetic sensor arrangement.

5. The system of claim 1 wherein the predetermined distance is a distance at least thee times greater than a greatest dimension of the first and the second permanent magnets.

6. The system of claim 5, the targeting array comprising:
   seventeen magnetic sensors with sixteen of the magnetic sensors being arranged about the seventeenth magnetic sensor that is centrally located within the sixteen magnetic sensors.

7. The system of claim 6, the targeting array comprising:
   five of the magnetic sensors being three channel magnetic sensors for measuring magnetic flux density in three orthogonal axes.

8. The system of claim 7, the targeting array comprising:
   twelve of the magnetic sensors being one channel only magnetic sensors for measuring magnetic flux density in only one axis of a three orthogonal axis system.

9. The system of claim 7 wherein one of the five magnetic sensors that are three channel sensors is centrally positioned within and equidistant from the other four of the five magnetic sensors.

10. The system of claim 1 further comprising:
    a display for indicating targeting array position with respect to the first permanent magnet at the distal end of the probe.

11. The system of claim 1 further comprising:
    a background magnetic sensor for measuring background magnetic fields so the background magnetic field measurements are removed from the measurements made with the targeting array.

* * * * *

UNITED STATES PATENT AND TRADEMARK OFFICE
CERTIFICATE OF CORRECTION

| | | |
|---|---|---|
| PATENT NO. | : 7,785,330 B2 | Page 1 of 1 |
| APPLICATION NO. | : 11/518775 | |
| DATED | : August 31, 2010 | |
| INVENTOR(S) | : Sherman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Fifteenth Day of February, 2011

David J. Kappos
*Director of the United States Patent and Trademark Office*